United States Patent [19]

Skinner et al.

[11] 4,081,328
[45] Mar. 28, 1978

[54] PRODUCTION OF CELLULASE BY A THERMOPHILIC THIELAVIA TERRESTRIS

[75] Inventors: Wilfred A. Skinner, Portola Valley, Calif.; Fumitake Tokuyama, Tokyo, Japan

[73] Assignee: Stanford Research Institute, Menlo Park, Calif.

[21] Appl. No.: 721,535

[22] Filed: Sep. 8, 1976

Related U.S. Application Data

[63] Continuation-in-part of Ser. No. 624,865, Oct. 23, 1975, abandoned.

[51] Int. Cl.$^2$ .................... C12D 13/10; C07G 7/02
[52] U.S. Cl. .................................. 195/62; 195/33; 195/66 R
[58] Field of Search ............... 195/33, 65, 66 R, 62, 195/81

[56] References Cited

U.S. PATENT DOCUMENTS 3,812,013  5/1974  Bellamy et al. ................. 195/66 R

OTHER PUBLICATIONS von Arx, Studies in Mycology, vol. 8, (1975), p. 10.
Hatt et al., The American Type Culture Collection Catalogue of Strains, 12th ed., (1976), p. 282.
Stutzenberger, "Cellulose Production by *Thermomonospora curvate* Isolated from Municipal Solid Waste Compost", Applied Microbiology, vol. 22, No. 2, (1971), pp. 147–152.
Knoesel et al., "Fungi from Compost of Waste Material, Enzymic Decomposition of Pectin and Cellulose by *Thermophilic species*", Chemical Abstracts, vol. 79, p. 161. Abs. No. 123441h (1973).
Flannigan et al., "Activities of *Thermophilus fungi* from Barley Kernels against Arabinoxylan and Carboxymethyl Cellulose", Chemical Abstracts, vol. 77, p. 222, Abs. No. 45327t (1972).
Dixon et al., Enzymes, Academic Press Inc., New York, 2nd ed. (1964), pp. 36, 37, 39–41.
Knoesel et al., "Pilze nus Mullkompost", Staedtehygiene, vol. 24, No. 6, (1973), pp. 143–148.
Smith et al., "Degradation of Arabinose in Wood Attacked by *Thermophilic Fungi*", Chemical Abstracts, vol. 78, No. 21, (1973), p. 157, abs No. 133512a.
Eslyn et al., "Changes in the Chemical Composition of Wood Caused by Six Soft–Rot Fungi", Chemical Abstracts, vol. 83. No. 1, (1975), p. 461, abs No. 5236e.

*Primary Examiner*—Raymond N. Jones
*Assistant Examiner*—Thomas G. Wiseman
*Attorney, Agent, or Firm*—Donovan J. De Witt

[57] ABSTRACT

A thermostable cellulase preparation exhibiting $C_1$ and $C_x$ cellulytic activities at a temperature from about 60° to about 70° C at a moderately acid pH from about 5.0 to about 5.6 is obtained by culturing the thermophilic fungus *Thielavia terrestris* (NRRL 8126) in a suitable cellulose-containing medium and recovering the cellulases thus produced.

8 Claims, 1 Drawing Figure

U.S. Patent     March 28, 1978     4,081,328
CURVES OF EXAMPLE 6
HEAT STABILITY OF CELLULASES PRODUCED
BY *THIELAVIA TERRESTRIS* AS DETERMINED BY HYDROLYTIC
ACTIVITY ON FILTER PAPER (FP)
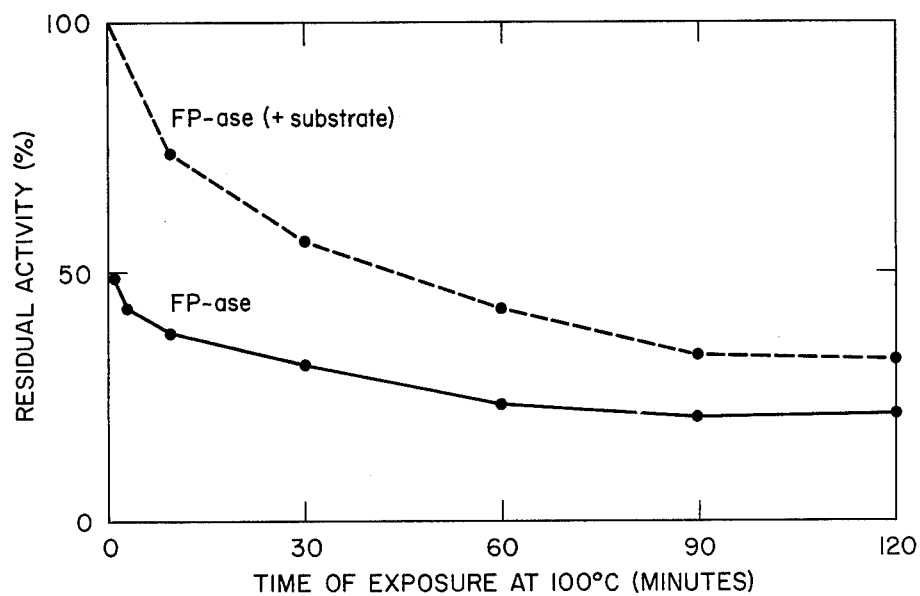

PRODUCTION OF CELLULASE BY A THERMOPHILIC THIELAVIA TERRESTRIS

CROSS-REFERENCE TO RELATED APPLICATION

This application is a continuation-in-part of application Ser. No. 624,865, filed Oct. 23, 1975, now abandoned.

BACKGROUND OF THE INVENTION

The invention described herein was made in the course of work under a grant or award from the Department of Health, Education and Welfare.

The present invention relates to the production and isolation of novel cellulases exhibiting optimum activity of the $C_1$ and $C_x$ types at temperatures in the range of about 60° to about 70° C and under moderately acid conditions, by the cultivation of the fungus *Thielavia terrestris* in a suitable cellulose-containing medium.

The term cellulase as employed hereinafter designates an enzyme complex capable of depolymerizing and hydrolyzing cellulose to glucose. Those cellulases known to the prior art have been produced either by fungi or by certain mold-like higher bacteria.

Various of these types of organisms have been shown to possess the ability to grow on a cellulose substrate. Many fungal cellulases are now commercially available. They are produced mostly by mesophilic fungi, i.e., those which will grow well at intermediate temperatures (25° to 37° C), and some of these cellulases exhibit relatively high $C_1$-enzyme type activity, meaning that they are capable of depolymerizing natural cellulose. The disadvantage of these fungal cellulases is that they cannot ordinarily be used to degrade cellulose at temperatures higher than about 50° C owing to their lack of heat stability.

Another type of cellulase activity is $C_x$-enzyme activity, measured by an ability to decompose carboxymethylcellulose (CMC). $C_1$ type activity is of primary commercial significance.

Cellulases produced by various organisms have been described in U.S. Pat. Nos. 3,232,832 (*Rhizopus*); 3,398,055 (*Trichoderma viride* ATCC 16325, and other fungi); 3,438,864 (Eumyces mold organism ATCC 16425); 3,677,899 (*Lampteromyces* or *Formitopsis*); and 3,734,831. However, cellulase preparations from Trichoderma viride, while known to be higher in $C_1$-enzyme activity than any other commercially available cellulases, have the drawback that the optimum temperature for their enzymic reactions is about 50° C (Mandels, et al. "Cellulases and Their Applications", ACS, Vol. 95, pp. 398–411 (1969)).

U.S. Pat. No. 3,812,013 discloses production of a soluble cellulase which is said to display optimum activity at pH levels from 5.5 to 8 at temperatures of 65° to 80° C, from a thermophilic actinomyces which is not otherwise specifically identified, and under conditions requiring the introduction of an oxygenating gas into the culture medium so as to maintain a minimum dissolved oxygen level therein. However, actinomyces are not true fungi, but are mold-like branching filamentary higher bacteria (Burdon and Williams, "Microbiology", 5th edition, 1964).

A publication by D. Knoesel and A. Resz, "Fungi from Compost of Waste Material", in Staedthygiene, 1973, 24(6), pp. 143–8; Chem. Abst. 79: 123441h (1973), discloses strains of numerous genera of thermophilic and thermotolerant fungi capable of decomposing natural cellulose, and suggests the presence of enzymes with $C_1$ and $C_x$ activities, including: Mucor, Absidia, Talaromyces, Dactylomyces, Myriococcum, Humicola, Thermoidium, Aspergillus, Paecilomyces, Scopulariopsis, and Acremonium.

F. J. Stutzenberger, Appl. Microbiol. 1971, 22(2), pp. 147–152; Chem. Abst. 75: 106381p (1971), mentions cellulase production by a cellulytic thermophilic actinomycete, *Thermonospora curvata*, at optimum of pH 6.0 and temperature 55° to 65° C.

B. Flannigan and P. N. Sellars, Trans. Brit. Mycol. Soc. 1972, 58 (pt. 2), pp. 338–341; Chem. Abst. 77: 45327t (1972) discloses the use of the thermophilic fungus *Thielavia sepedonium* P101 to hydrolyze carboxymethylcellulose, but does not describe the production of a cellulase(s) therefrom, or its (their) properties.

SUMMARY OF THE INVENTION

In accordance with a first aspect of the present invention, it has been found that a thermostable cellulase exhibiting both $C_1$ and $C_x$ types of cellulytic activities is produced by the fungal organism *Thielavia terrestris* (NRRL 8126). This fungus is thermophilic, meaning that it exhibits optimum growth at a temperature in the range from about 60° to about 90° C. As will be described more fully below, the fungus is cultivated in a liquid medium containing assimilable carbon and nitrogen sources, and growth promoting co-factors.

*Thielavia terrestris* is a known fungus of soil origin, and was originally designated as *Allescheria terrestris* by Apinis, Nova Hedwigia 5: 68 (1963). A study of *Thielavia terrestris* by Malloch and Cain, Can. J. Bot. 50: 66 (1972) showed it to be the same organism. It was found to occur in the conidial state by Minoura et al., Trans. Mycol. Soc. Japan, 14: 362 (1973).

Our organism has been taxonomically studied by J. A. von Arx of the Centraalbureau voor Schimmelcultures, Baarn, The Netherlands (CBS), and he reported that it fit the description he published in the publication of that organization "Studies in Mycology 8", page 10 (January 1975). It is as follows:

"No ascomata could be observed in the type strain. The aerial mycelium is composed of hyaline or light brownish, regularly septate, 2–4 μm broad hyphae with often partly swollen cells. The conidiogenous cells arise as short, lateral branches on the hyphae and may elongate during the formation of the conidia. The conidia are broadly clavate, obovate or pyriform, with a truncate base, 1-celled, hyaline, 3–6 × 2–3 μm, and are borne singly, in basipetal succession or in indistinct sympodulae.

"Ascomata developed in CBS 492.74 on malt-agar at 36° C beneath the lanose mycelial mat. They are spherical or slightly flattened, usually smooth, black, 140–280 μm in diameter, with an 8–10 μm thick wall composed of thick-walled, dark brown, 2–3 μm broad, irregularly interwoven hyphal cells (loose *Textura epidermoidea*). The asci develop in fascicles from croziers, are clavate, stalked, 8-spored, 20–27 × 9 × 12 μm, evanescent. The ascospores are ovate or pyriform, brown, thick-walled, contain 1–2 droplets, have a distinct germ pore at the attenuated end and measure 5.5–7 × 4–5.5 μm.

"The conidial state may be close to genera such as Scopulariopsis and especially Scedosporium and this points to a relationship with the Microascaceae."

A culture of the *Thielavia terrestris* organism has been deposited in the culture collection of the Northern Regional Research Laboratories, Agricultural Research Service, U.S. Department of Agriculture, Peoria, Illinois 61604, and it has been assigned the number NRRL 8126.

As carbon sources, a variety of cellulosic materials may be employed such as cellulose powder, absorbent cotton, wheat bran, newsprint, cotton gin trash, and bagasse. The nitrogen source may be inorganic or organic nitrogen consisting of materials such as ammonium salts, nitrates, corn steep liquor, yeast extract peptone, yeast cells, and the like. Conventional mineral nutrients such as salts of boron, iron, copper, manganese and zinc, are also incorporated in the culture medium. Growth promoting factors may also be added, such as biotin (vitamin H) and other vitamins. As a practical matter, biotin-containing organic materials such as corn steep liquor, yeast extract, and the like can be used to serve for both the growth factor and as a nitrogen source.

For the cultivation of *Thielavia terrestris*, primary cultures are usually started by transferring a small amount of mycelium from stock cultures. Primary cultures are used as inocula for jar fermentations. Preferred temperatures for growth of the organism range from about 40° to about 50° C, and a preferred pH range for this purpose is from about 4.5 to about 6.0. The initial pH of the medium is typically about 5.6 and is controlled at this level by adding either acid or base. After cultivation for 36 to 48 hours, during which the system evidences a maximum yield of cellulase, the enzyme solution is collected by either centrifugation or filtration, the filtrate representing the crude enzyme material. The culturing conditions are dependent upon the type of medium used and should, of course, be those resulting in a maximum yield of cellulase.

The crude enzyme solution thus recovered can be treated with ammonium sulfate at about 4° C to precipitate the cellulase. The resulting precipitate is collected by centrifugation and is then dissolved in pH 5 acetate buffer of suitable concentration. Both the crude and the concentrated enzyme solutions show high $C_1$ activity. Further, both are stable for at least 3 weeks at 4° C, and they can be usefully employed at temperatures of about 60° to 65° C and even higher, e.g. 70° C, under desirably moderate pH conditions, namely from about 5.0 to about 5.6.

The present invention thus provides a method for the concentration of cellulase activity from *Thielavia terrestris* (NRRL 8126) fermentations by precipitation of the enzymatic activity from culture filtrates with additions of salts, separation of the precipitate and dissolving this product in suitable buffer or producing a dried preparation from the salt precipitated product.

In accordance with a second aspect of the invention, the cellulases produced by *Thielavia terrestris* have been isolated, and the characteristics and properties discovered. The cellulases are water-soluble solids, precipitable by ammonium sulfate, and can be dissolved in suitable buffers. The preparations possess both $C_1$ and $C_x$ enzyme activity. They exhibit optimum cellulytic activity at temperatures from about 60° to about 70° C under moderately acid conditions of pH from about 5.0 to about 5.6, and retain their activity for a period of at least 48 hours.

Another characteristic of the cellulases of the invention is their high degree of stability toward heat. Thus, after boiling a crude enzyme water solution for three hours, 20% of the enzyme activity still remains, unlike any cellulase previously reported. Moreover, it has been found that at 100° C, in the presence of a cellulose substrate, e.g. filter paper which is hydrolyzed to glucose, the preparation retains 50% of its hydrolytic activity after 60 minutes and 30% after 120 minutes. These features are reviewed in Example 6 and its accompanying drawing.

The cellulase preparations possess strong $C_1$-activity toward natural celluloses. Thus, the crude enzyme preparations can hydrolyze cotton to the extent of 20% within 24 hours at 60°–65° C at pH 5.0.

These properties provide several practical advantages when the cellulases of the invention are employed in the hydrolysis of cellulosic materials, for which they possess special utility. Among these, and other advantages, are: (1) minimizing of undesirable microbial contamination and the use of expensive sterilized substrates and conditions by conducting the reactions at elevated temperatures and low pH, with resultant lower operating costs; (2) higher reaction rates at lower operating temperatures; and (3) in the production of the enzymes from the termophilic organism of the invention, a higher temperature can be used, thus reducing cooling costs associated with processes of the prior art employing mesophilic organisms which would be unstable at high temperatures.

As indicated in the preceding paragraphs, it is a feature of the present invention that the stability of the present *Thielavia terrestris* cellulases to heat makes it possible by heating the system, to effect simultaneous destruction of undesirable enzymes that may be present and the preservation of a substantial portion of the cellulase activity. Exemplary enzymes that can be destroyed in this fashion include those causing such undesirable effects as protein hydrolysis, various deaminations, hydrolysis of lipids and the like.

The present invention thus provides a process for treating an aqueous system containing *Thielavia terrestris* (NRRL 8126) cellulases as well as enzymes of an undesirable character, said process comprising the step of heating said system to elevated temperatures capable of destroying said undesirable enzymes without fully destroying the activity of the cellulases.

The cellulases produced by *Thielavia terrestris* are active on most cellulosic substrates. For example, the present cellulase preparations can convert 20% of whole cotton fibers, which are considered very resistant to digestion, to glucose at 60° C within a 24 hour period. This is in contrast with the use of ground cotton fibers that are most susceptible to hydrolysis. This value is much higher than that obtainable with *Trichoderma viride* enzymes, generally considered as the best presently available.

The principle of the cellulase reaction is to depolymerize cellulose ultimately to glucose, which is known to be a good carbon source. Glucose is both an important food material and one which can readily be converted to other compounds such as methane and ethanol which are also good energy sources.

The cellulases of the invention, when used either alone or in conjunction with other enzymes, also have a wide variety of other applications. These include use as a digestive aid, as an aid in the clarification and extraction of fruit juices, and utility in the handling of paper-pulp fibers in that they decrease the necessary beating time while also contributing to the improved qualities of the resultant paper. The cellulase product can be used to break down cell walls of yeast, cereals, and many other food products to enhance digestibility of these products by man and other animals. Further, among other applications, these cellulases can be used to remove fiber from edible oil seed cakes, and to increase the agar-agar yield from seaweed.

DESCRIPTION OF THE PREFERRED EMBODIMENTS

The following examples are illustrative of preferred embodiments of the invention, but are not to be considered as limiting the invention thereto:

EXAMPLE 1

Stock cultures of *Thielavia terrestris* (NRRL 8126) were maintained on agar slants containing 1% cellulose powder and other essential nutrients. Primary cultures were prepared by transferring a small amount of mycelium to a 225 ml flask containing 100 ml of medium. Precultures were also prepared by transferring mycelium from liquid culture.

Precultures were grown for 24 hours in shaker flasks at 45° to 48° C and used as inocula for the jar fermentations. The medium composition for fungal growth and cellulase production is as follows:

| Component | g/l H$_2$O |
| --- | --- |
| KH$_2$PO$_4$ | 6.8 |
| (NH$_4$)$_2$SO$_4$ | 1.3 |
| MgSO$_4$ . 7H$_2$O | 0.5 |
| CaCl$_2$ | 0.2 |
| Trace element solution | 2 ml (see below) |
| Cellulose powder | 10 |
| Peptone | 1.5 |
| Corn steep liquor | 2 |
| pH adjusted at 5.5 | |

| Trace Element Solution (mg/100 ml) | |
| --- | --- |
| H$_3$BO$_3$ | 6 |
| (NH$_4$)$_6$MoO$_{24}$ . 4H$_2$O | 26 |
| FeCl$_3$ . 6H$_2$O | 100 |
| CuSO$_4$ . 5H$_2$O | 40 |
| MnCl$_2$ . 4H$_2$O | 8 |
| ZnCl$_2$ | 200 |

During fermentation the pH was maintained between 5.5 and 5.6. Air was supplied during the fermentations. Temperature was maintained at 48° C. The $C_1$ and $C_x$ type enzyme activities were determined by tests conducted periodically over the ensuing 46 hour jar-fermentation step, the first tests being made at the start of said period.

For the enzyme activity tests, small samples of the contents of the jar were centrifuged and the desired supernatant liquids were used in making activity tests by the methods of Mandels et al. "Enzymatic Hydrolysis of Waste Cellulose", Biotechnology and Bioengineering, Vol. 16, pp. 1471-1493 (1974), but using an incubation temperature of 60° rather than 50° C. More particularly, the FP (filter paper) test, used to determine $C_1$ activity, was carried out by incubating a small amount of said supernatant along with 0.5M acetate buffer, pH 5.0, the respective volumes being 0.5 ml of the supernatant and 1.0 ml of the buffer in the tests conducted at 0 hours, with progressively smaller amounts of the supernatant liquid being employed at the various downstream fermentation times indicated in the table below.

In each case, however, the amount of the buffer employed was increased to compensate for the smaller volumes of the samples, so that the total volume remained at 1.5 ml. Test incubations were conducted for one hour at 60° C using a 50 mg strip (1 × 6 cm) of Whatman No. 1 filter paper. The resultant glucose level was measured by adding dinitrosalicylic acid reagent and calculating the reducing sugar as glucose. The values thus obtained were recalculated so as to express the glucose level in terms of that amount prevailing in 1.0 ml of the recovered fermentation supernatant at the indicated incubation time.

$C_x$ values were also determined by using 0.5 ml of the supernatant liquid at 0 hours in the jar-cultivation process and with progressively smaller quantities as the cultivation continued. The supernatant was made up to 1 ml, in each case, by addition of the acetate buffer. In each case the buffered sample was combined with 0.5 ml of a 1% buffered carboxymethylcellulose (CMC) solution. The resulting system was incubated for 30 minutes at 60° C. It was then tested for glucose content which was then expressed in terms of the content of glucose in 1.0 ml of the fermentation supernatant. The values obtained in a typical fermentation are set forth in the following table:

| Cultivation Time (hours) | Cellulase Activity (mg glucose/ml enzyme) | |
| --- | --- | --- |
| | FP | CMC |
| 0.0 | 0.2 | 0.8 |
| 15.0 | 1.5 | 12.8 |
| 18.0 | 2.8 | 23.0 |
| 22.0 | 5.2 | 58.0 |
| 26.5 | 8.0 | 76.0 |
| 30.5 | 9.6 | 87.0 |
| 40.5 | 12.2 | 89.0 |
| 46.0 | 12.0 | 89.0 |

EXAMPLE 2

In this operation the incubation was performed as described in Example 1, except that the peptone and corn steep liquor present in the composition employed for cellulase production were replaced by 10 μm of biotin per liter of said composition. The following FP values were obtained, the method employed being that described in Example 1:

| Cultivation Time (hours) | FP Cellulase Activity (mg glucose/ml enzyme) |
| --- | --- |
| 0 | 0.1 |
| 18 | 0.1 |
| 24 | 2.0 |
| 30 | 4.0 |
| 41 | 9.2 |
| 48 | 11.6 |

EXAMPLE 3

Shaker flasks were used to produce cellulases on the various substrates shown in the following table, the media composition being otherwise the same as in Example 1. The temperature was maintained at 48° C during the incubation period and pH levels were uncontrolled. Initial pH was 5.5 and final pH ranged from 5.5 to 6.2.

| Culture Substrate | FP Activity at 46 Hours (mg glucose/ml enzyme) |
| --- | --- |
| Newsprint | 8.0 |
| Bagasse | 5.4 |
| Cotton gin trash | 5.0 |
| Wheat bran | 3.2 |

| Culture Substrate | FP Activity at 46 Hours (mg glucose/ml enzyme) |
| --- | --- |
| Cellulose powder | 5.0 |

EXAMPLE 4

At the conclusion of the 46 hour cultivation period in Example 1, an enzyme solution was recovered by filtration. The filtrate was maintained at about 4° C and then ammonium sulfate added to 75% saturation. The resulting precipitate was collected by centrifugation and dissolved in 0.5 M acetate buffer, pH 5.0. Filter paper cellulase activity was equal to 98 mg glucose per ml of enzyme solution.

EXAMPLE 5

Following the general procedure of Example 1, the cellulase activity was tested at 60° C for 24 hours against various cellulosic materials employing the crude ammonium sulfate precipitated enzyme preparation. In each case the cellulose activity was measured by the per cent conversion of the substrate to glucose, the results obtained being summarized in the following table:

| Substrate | Cellulase Activity (% conversion to glucose) |
| --- | --- |
| Cellulose powder (Avicel 105) | 52.0 |
| Solka floc SW40 | 39.0 |
| Newsprint | 28.0 |
| Filter paper | 38.0 |
| Absorbent cotton | 14.0 |
| Bagasse | 2.9 |

EXAMPLE 6

The stability toward heat of the cellulase in aqueous solution both by itself, and in the presence of a cellulosic substrate (filter paper) was tested. In the accompanying drawing, the curve marked "FP-ase" shows the percentage of retained activity upon maintaining the enzyme solution at boiling temperature (100° C) for various time intervals. Thus, even after maintaining the enzyme solution at 100° C for 3 hours, 20% of the enzyme activity still remains. This is unlike the stability of any previously described cellulase preparation. Moreover, as shown in the curve marked "FP-ase (+ substrate)", it has been found that at 100° C, in the presence of a filter paper cellulose substrate which hydrolyzes to glucose, the preparation retains 50% of its hydrolytic activity after 60 minutes and 30% after 120 minutes.

What is claimed is:

1. A cellulase enzyme preparation produced by the fungus *Thielavia terrestris* (NRRL 8126), which is a water-soluble solid, precipitable by ammonium sulfate, possesses both $C_1$ and $C_x$ types of enzyme activity and a high degree of stability toward heat, and exhibits optimum enzyme activity at a temperature from about 60° to about 70° C at a pH between about 5.0 and about 5.6.

2. A method for the production of a cellulase enzyme by the fungus *Thielavia terrestris* (NRRL 8126), which comprises culturing said fungus in a nutrient medium therefor and recovering the enzyme produced.

3. The method of claim 2 in which said medium includes a cellulosic substrate.

4. The method of claim 2 in which the culture is carried out at a temperature between 40° and about 50° C at a pH between about 4.5 and about 6.0.

5. The method of claim 2 in which said medium contains sources of assimilable carbon and nitrogen, and a growth promoting factor.

6. The method of claim 5 in which growth promoting factor is biotin.

7. A method for the concentration of cellulase activity from *Thielavia terrestris* NRRL 8126 fermentations, comprising the steps of precipitating the enzyme activity from culture filtration with addition of salts, separating the resulting precipitate and either dissolving this precipitate product in a suitable buffer or converting said product to a dried preparation.

8. A process for treating an aqueous system containing *Thielavia terrestris* (NRRL 8126) cellulases as well as enzymes of an undesirable character, said process comprising the step of heating said system to elevated temperatures capable of destroying said undesirable enzymes without fully destroying the activity of the cellulases,

* * * * *